United States Patent [19]
Lynch et al.

[11] Patent Number: 5,962,244
[45] Date of Patent: Oct. 5, 1999

[54] HIGH-THROUGHPUT IN VITRO ASSAYS FOR MODULATORS OF PEPTIDYL TRANSFERASE

[75] Inventors: Anthony Simon Lynch, Pacifica; Michael Gregory Peterson, Millbrae; Binoj Joseph Matthew, Los Angeles, all of Calif.

[73] Assignee: Tularik Inc., South San Francisco, Calif.

[21] Appl. No.: 09/074,580

[22] Filed: May 7, 1998

[51] Int. Cl.⁶ .............................. C12Q 1/48; C12Q 1/00; G01N 33/53

[52] U.S. Cl. .............................. 435/15; 435/4; 435/7.72; 435/7.71; 435/68.1; 435/69.2; 435/183; 530/300; 536/23.1; 536/18.5

[58] Field of Search .................... 435/15, 4, 7.72, 435/7.71, 68.1, 69.2, 183; 530/300; 536/23.1, 18.5

[56] References Cited

U.S. PATENT DOCUMENTS 5,643,722  7/1997  Rothschild et al. ................. 435/6
5,801,013  9/1998  Tao et al. ............................ 435/69.1

OTHER PUBLICATIONS

Ravel et al, Biochem, vol. 9 (25), pp. 5028–5033, 1970. Month Not Available. Please Print.

*Primary Examiner*—Louise N. Leary
*Attorney, Agent, or Firm*—Townsend and Townsend and Crew LLP

[57] ABSTRACT

High-throughput in vitro assays are provided for identifying modulators of peptidyl transferase. New solid-phase assays, related compositions, apparatus and integrated systems are provided.

29 Claims, 9 Drawing Sheets

Peptidyl Transferase - Fragment Reaction

Analyze by paper chromatography

Peptidyl Transferase - Fragment Reaction

Analyze by paper chromatography

Peptidyl Transferase
HTS Assay Format 2

Necessary reagents:

Peptidyl Transferase
HTS Assay Format 1: data

Peptidyl Transferase
HTS Assay Format 1: data
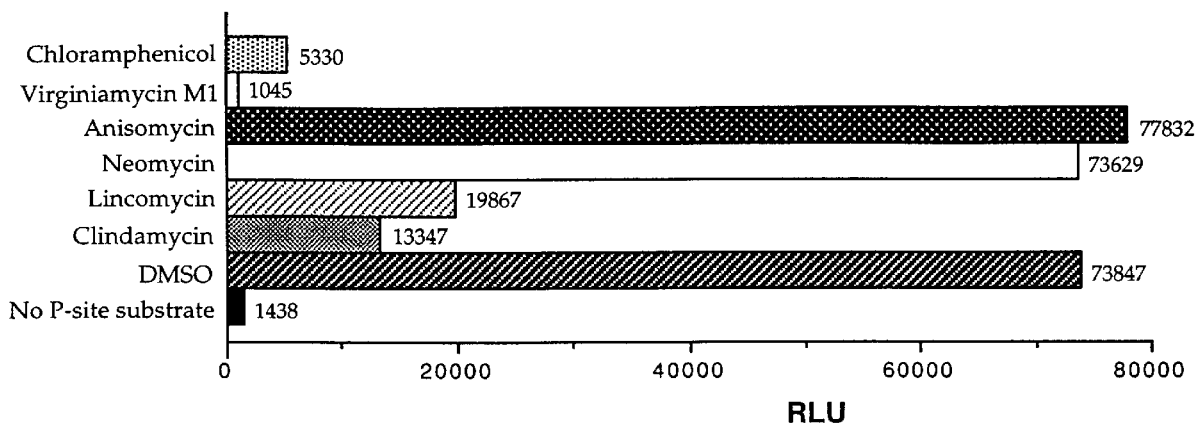
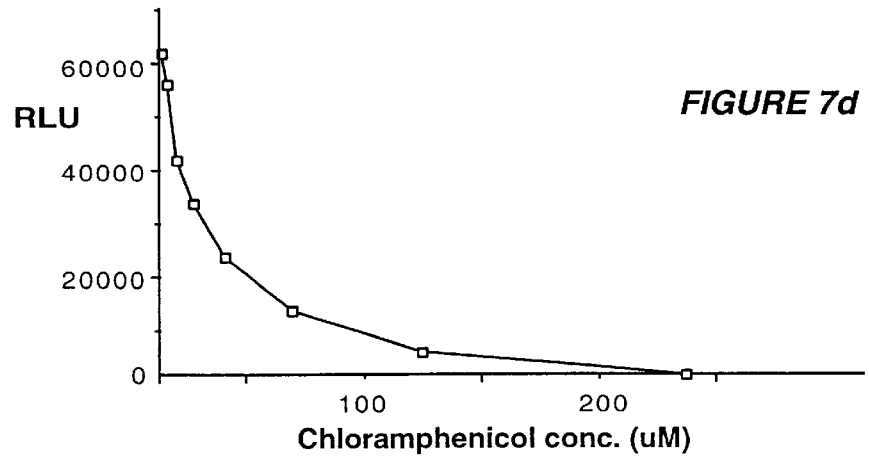
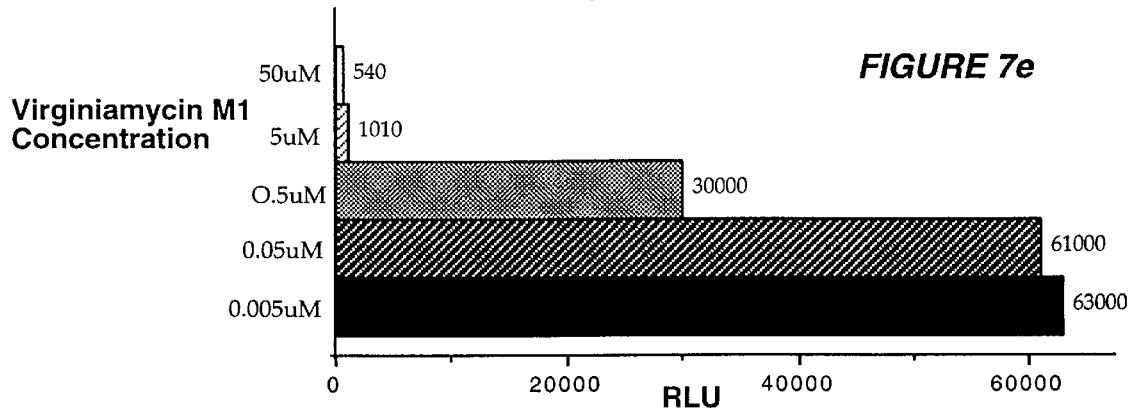

Peptidyl Transferase
HTS Assay Format 2: data

HIGH-THROUGHPUT IN VITRO ASSAYS FOR MODULATORS OF PEPTIDYL TRANSFERASE

FIELD OF THE INVENTION

The present invention relates generally to high-throughput in vitro assays for identifying modulators of peptidyl transferase activity. New solid phase assays, related compositions, apparatus and integrated systems are provided.

BACKGROUND OF THE INVENTION

Protein synthesis is carried out by an elaborate translation complex, which is composed of a ribosome, accessory protein factors as well as mRNA and charged tRNA molecules. Like DNA and RNA synthesis, protein synthesis can be divided into initiation, chain elongation and termination stages. Initiation involves the assembly of the translation complex at the first codon in the mRNA. During polypeptide-chain elongation, the ribosome and associated components move in the 5' to 3' direction along the template mRNA. The polypeptide is synthesized from the N-terminus to the C-terminus. Finally, when synthesis of the protein is complete, the translation complex disassembles in a separate termination step. An important part of this disassembly is the release of the ribosome from the mRNA.

Catalysis of peptide bond formation requires the precise juxtaposition by the ribosome of the acceptor ends of the amino acid-charged tRNA's bound in the peptidyl site (i.e., P site) and aminoacyl site (i.e., A site) of its "active site". This activity represents the essential enzymatic activity of the ribosome and is referred to as the "peptidyl transferase activity," an integral component of the large subunit of all ribosomes characterized to date. Studies of bacterial ribosomes have identified the essential active site constituents of the peptidyl transferase activity as a few ribosomal protein subunits and the 23S rRNA. As the integrity of the latter is essential for enzymatic activity, it is assumed that it plays a direct role in the catalysis of peptide bond formation acting as a so-called ribozyme.

A key step in characterizing the peptidyl transferase reaction was achieved by development of the so-called fragment reaction, wherein the P-site aminoacyl-tRNA is replaced by a small-molecule derivative (e.g., 5'-CAACCA-formyl methionine) and the A-site aminoacyl-tRNA is replaced by puromycin (which mimics the 3' terminus of an aminoacyl-tRNA). During the course of the reaction, which is illustrated diagrammatically in FIG. 1, the amino group of puromycin forms a peptide bond with fMet to yield an fMet-puromycin product. Characterization of this simple reaction, which isolates this phase of the overall translation elongation cycle from other steps (e.g., binding of aminoacyl-tRNA's, release of free tRNA's, and mRNA binding and translocation), allowed for the delineation of the protein and RNA components of the ribosome as well as cofactors required specifically for the peptide bond formation step during elongation. Further studies established the authenticity of the fragment reaction as a valid model of normal peptide bond formation reactions in vivo by demonstrating inhibition of this reaction by antibiotics that have been demonstrated to act at this level in whole cells.

A large number of antibacterial agents, including many in current clinical use, inhibit protein synthesis in bacteria by interfering with essential functions of the ribosome. When ribosomal function is perturbed, protein synthesis may cease entirely or, alternatively, it may be sufficiently slowed so as to stop normal cell growth and metabolism. Differences between the prokaryotic 70S ribosomes (composed of 50S and 30S subunits) and the eukaryotic 80S ribosome (composed of 60S and 40S subunits) underlie the basis for the selective toxicity of many antimicrobial agents of this class. However, a limited subset of this class of antimicrobial agents exhibits some cross-reactivity with the 70S ribosomes of eukaryotic mitochondria. This cross-reactivity probably accounts for the host cells cytotoxicity effects observed with some agents and has limited their use as clinical antimicrobial agents. Other agents (e.g., tetracycline), which affect the function of eukaryotic 80S ribosomes in vitro, are still used clinically to treat bacterial infections as the concentrations employed during antimicrobial therapy are not sufficient to elicit host cell toxicity side-effects.

Moreover, protein biosynthesis inhibitors can be divided into a number of different classes based on differences in their mechanisms of action. The aminoglycoside agents (e.g., streptomycin) bind irreversibly to the 30S subunit of the ribosome, thereby slowing protein synthesis and causing mis-translation (i.e., mis-reading) of the mRNA. The resulting errors in the fidelity of protein synthesis are bacteriocidal, and the selective toxicity of this family of agents is increased by the fact that bacteria actively transport them into the cell. The tetracycline family of agents (e.g., doxycycline) also binds to the 30S ribosome subunit, but does so reversibly. Such agents are bacteriostatic and act by interfering with the elongation phase of protein synthesis by inhibiting the transfer of the amino acid moieties of the aminoacyl-tRNA substrates into the growing polypeptide chain. However, inhibition mediated by the tetracyclines is readily reversible, with protein synthesis resuming once intracellular levels of the agent's decline. Chloramphenicol and the macrolide family of agents (e.g., erythromycin), in contrast, act on the function/activity of the 50S subunit of the ribosome. These agents are bacteriostatic in nature, and their effects are reversible. Finally, puromycin acts as a competitive inhibitor of the binding of aminoacyl-tRNA's to the so-called aminoacyl site (i.e., A-site) of the ribosome and acts as a chain-terminator of the elongation phase as a result of its incorporation into the growing peptide chain.

Shortcomings with previously available assays for peptidyl transferase activity have hampered the search for novel modulators of peptidyl transferase activity. For example, many previously available assays require the use of radioactive compounds and/or suffer from a lack of sensitivity. Moreover, previously available assays for peptidyl transferase activity are not amenable to high throughput screening methods such as are needed to screen large libraries or groups of potential modulators. Thus, there remains a need in the art for new assay methods for identifying modulators of peptidyl transferase activity. The present invention remedies this and other needs.

SUMMARY OF THE INVENTION

High-throughput assays for identifying modulators of peptidyl transferase are provided. Both inhibitors and activators of peptidyl transferase activity can be screened using the assays of the present invention. Solid phase throughput assays are provided, as are related assay compositions, integrated systems for assay screening and other features that will be evident upon review.

In one aspect, high-throughput in vitro assays for peptidyl Transferase activity are provided. In such assays, a reaction mixture containing a peptidyl trarnsferase, a peptidyl-tRNA analog, which comprises a peptidyl moiety and an immobilizable tag, and an aminoacyl-tRNA analog is incubated under conditions suitable for transfer of the peptidyl moiety to the aminoacyl-tRNA analog. The reaction mixture is contacted with a solid support to which the immobilizable tag of the peptidyl-tRNA analog can be bound or immobilized. The solid support is washed and, thereafter, the presence, absence or amount of the aminoacyl-tRNA analog bound to the solid support is determined either directly or indirectly. In a presently preferred embodiment, a potential modulator of peptidyl transferase activity is also added to the reaction mixture and the effect of the modulator on the peptidyl transferase activity is determined.

One of the advantages of the present invention is that intact ribosomes or, alternatively, 23s rRNA plus ribosomal subunits to which the peptidyl transferase has been localized can be employed. In a preferred embodiment, the peptidyl transferase comprises 23S rRNA. The 23S rRNA further comprises either an intact prokaryotic ribosome or, alternatively, the 50S subunit of the prokaryotic ribosome. In another preferred embodiment, the peptidyl transferase comprises 28S rRNA. The 28S rRNA comprises either an intact eukaryotic ribosome or, alternatively, the 60S subunit of the eukaryotic ribosome. Moreover, numerous peptidyl-tRNA analogs and aminoacyl-tRNA analogs can be used in the assays of the present invention. In a preferred embodiment, the peptidyl-tRNA analog is an amino acid conjugated to an oligonucleotide. In a more preferred embodiment, the peptidyl-tRNA analog is 5'-CACCA-phenylalanine or 5'-CCA-phenylalanine. Moreover, in a preferred embodiment, the aminoacyl-tRNA analog is puromycin and is directly detectable.

Using the high-throughput screening assays of the present invention, novel inhibitors of the peptidyl transferase activity of bacterial and fungal ribosomes can be identified that are of potential use in the development of antibacterial and antifungal agents. Such agents would be of significant clinical value as therapeutic agents in the treatment of infectious diseases, as target-based resistance to such agents is not anticipated to occur at high frequency. For instance, as the gene encoding the 23S rRNA component of the prokaryotic ribosome is present in copy numbers of 2–7 per genome (with a copy number of >5 typical in eubacterial pathogen species), effective resistance to novel agents mediated by mutations in the 23S rRNA component may not arise due to the requirement to accumulate the resistance mutation(s) in all (or at least a majority) of the chromosomal gene copies. Moreover, as agents that inhibit protein biosynthesis do so by affecting numerous different discrete steps within the overall process, such agents provide valuable research tools in elucidating the biochemistry and enzymology of protein synthesis in both prokaryotic and eukaryotic systems.

In another aspect, the present invention provides kits, compositions and integrated systems for performing the assays disclosed herein.

Other features objects and advantages of the invention and its preferred embodiments will become apparent from the detailed description that follows.

BRIEF DESCRIPTION OF THE DRAWINGS

FIGS. 7a–7d demonstrate the efficacy of the assay illustrated in FIG. 3 and its ability to identify novel inhibitors of the peptidyl transferase activity. FIG. 7a demonstrates the dependence of the assay on the addition of each of the major components. FIG. 7b demonstrates the dependence of the assay on the concentration of P-site substrate. FIGS. 7c–7e demonstrate the sensitivity of the assay to a range of known inhibitors of the peptidyl transferase reaction, and the insensitivity of the assay to other antibiotics which inhibit protein translation via effects on other components of the translational machinery.

FIGS. 8a and 8b demonstrate the dependence of the assay on the addition of each of the major components and the sensitivity of the assay to the inclusion of known peptidyl transferase inhibitors (i.e., chloramphenicol and virginiamycin M1). FIG. 8c provides data that verifies the integrity of the peptidyl transferase reaction product (i.e., $^{32}$P-C-puromycin-(N)-biotin-phenylalanine) formed during the reactions illustrated in FIG. 8b.

DETAILED DESCRIPTION OF THE INVENTION AND PREFERRED EMBODIMENTS

A. General Overview

Figure 1:
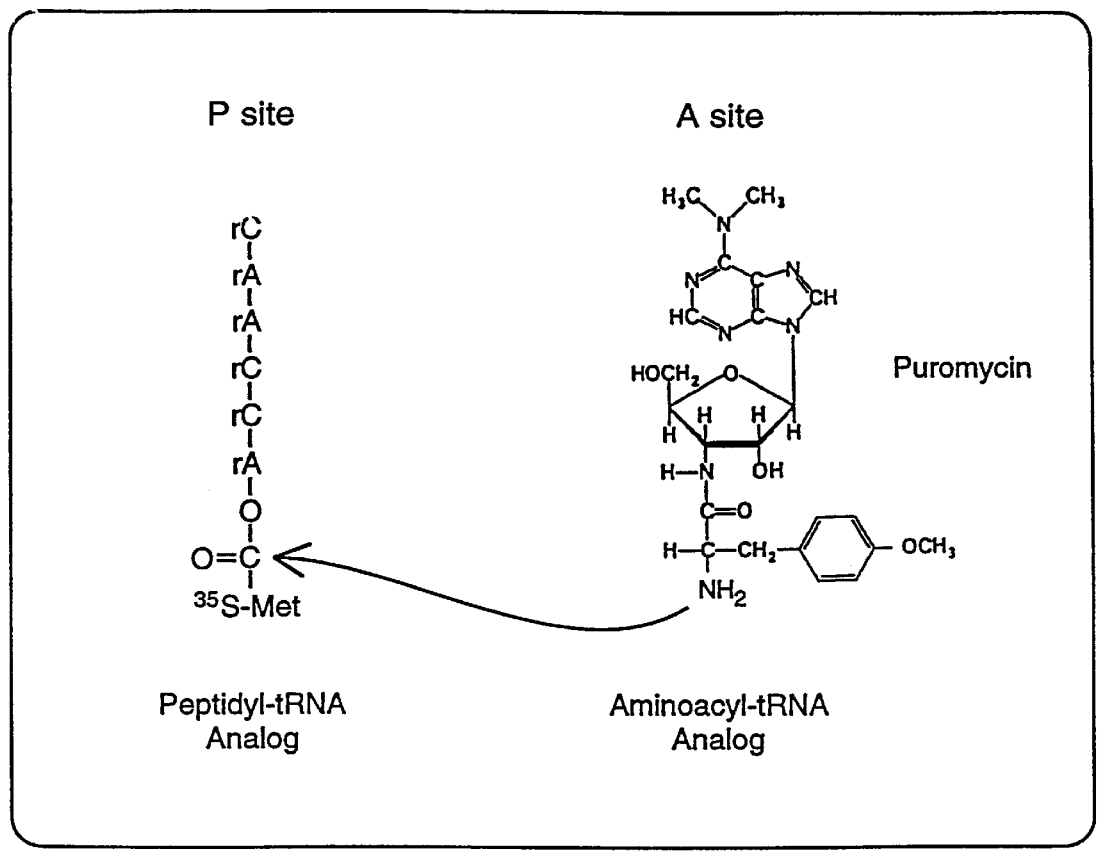
FIG. 1 illustrates diagrammatically the "fragment reaction." In this reaction, a peptide bond is formed between puromycin at the A-site of a ribosome and the nascent peptide bound to the tRNA in the P-site. The product of this reaction is bound only weakly in the A-site and dissociates from the ribosome, thus terminating protein synthesis and producing an incomplete, inactive peptide.
Figure 1:
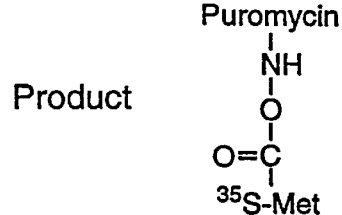

The present invention provides solid phase assays for measuring the activity of peptidyl transferase in the presence of a peptidyl transferase activity modulator. High throughput methods, compositions, kits and integrated systems are provided for detecting peptidyl transferase activity in vitro and for measuring the effect of potential modulators of peptidyl transferase activity. Accordingly, the assays of the present invention have, inter alia, at least two immediately useful properties. First, the assays can be used to detect peptidyl transferase activity in vitro, serving as a replacement for standard cell-free assays that target protein synthesis in general. As such, the assays provide broadly applicable tools for assessing peptidyl transferase activity in a high-throughput format.

Second, the assays provide for the identification of modulators of peptidyl transferase activity. Such modulators are valuable research tools that can be used to elucidate the biochemistry and enzymology of protein synthesis in both prokaryotic and eukaryotic systems. Moreover, such modulators provide lead compounds for drug development to treat a variety of conditions, including the development of the drugs useful as antibacterial, antifungal, inflammation modulatory, or immune system modulatory agents. Accordingly, the assays of the present invention are of immediate value as a result of their ability to identify lead compounds for pharmaceutical and/or other research applications. Moreover, such assays are particularly well suited to high throughput automation, making them especially valuable for their ability to identify lead compounds.

More particularly, the assays of the present invention, which specifically target the peptidyl transferase activity of the ribosome and which can employ whole ribosomes, have a number of advantages over typically used cell-free assays that target protein synthesis in general. Such advantages include, but are not limited to, the following. First, there is no requirement that radioactive reagents be employed (although they are optionally used as discussed below). Second, the assays of the present invention target a specific, but essential step in the overall translation cycle. This specificity will, in turn, significantly enhance the rapidity by which novel inhibitory agents can be characterized at the mechanistic level. Third, the assays of the present invention can utilize ribosomes of any origin. This feature of the assays greatly facilitates experiments designed to establish the specificity of novel agents. For instance, human cell derived ribosomes can be employed in a counter-screen assay to identify agents that may be expected to be cytotoxic due to their effects on the human peptidyl transferase activity. Fourth, the assays can be performed in the solid-phase. Fifth, other than the optionally employed immune detection reagents, there is no requirement to employ additional enzymatic components in the assay. Sixth, the assays employ simple reagents that can be readily synthesized and obtained in the quantities needed for high-throughput screening in a modem drug discovery system. Finally, any of the assay formats described herein is readily amenable for automation and high-throughput ("HTS") using current reagents, devices and methodologies.

Further, several aspects of the discovery were surprising. First, kinetic analysis of the peptidyl transferase reaction using the substrates employed in the HTS assays of the present invention suggested that the assay reactions occur under multiple enzymatic turnover conditions. In the absence of the latter, the effective signal detection window of the assays would have been expected to be so low as to considerably limit the potential of the assay for HTS. Second, the assay formats utilizing either radioisotopic or immune-based detection methodologies are particularly sensitive and enable one to use limited quantities of the P-site substrate. Third, it has been determined that relatively crude preparations of ribosomes (e.g., prokaryotic or eukaryotic ribosomes) can be used in the assays of the present invention so that the scale-up preparation of this component for the HTS assays does not represent a problem. Fourth, the behavior of known protein synthesis inhibitors in the assays of the present invention demonstrates that such assays are very specific and sensitive to known agents that target the peptidyl transferase activity. Finally, essentially equivalent results are obtained using ribosome preparations made from a range of different sources (e.g., bacteria), indicating that the assays can be utilized to find inhibitors of peptidyl transferase activities from any source.

B. Reaction Components

In the assays of the present invention, a reaction mixture comprising a peptidyl transferase, a peptidyl-tRNA analog and an aminoacyl-tRNA analog are incubated under conditions suitable for transfer of the peptidyl moiety of the peptidyl-tRNA analog to the aminoacyl-tRNA analog. The peptidyl-tRNA comprises a peptidyl moiety and an immobilizable tag, whereas the aminoacyl-tRNA analog is capable of being detected either directly or indirectly. In a presently preferred embodiment, the reaction mixture further comprises a potential modulator of peptidyl transferase activity. If peptidyl transferase activity is present and uninhibited, it catalyzes the transfer of the peptidyl moiety of the peptidyl-tRNA analog to the free amino group of the aminoacyl-tRNA analog. The peptidyl-aminoacyl-tRNA analog is weakly bound in the A site and soon dissociates from the ribosome, thereby terminating protein synthesis and producing an incomplete, inactive peptide.

Figure 2:
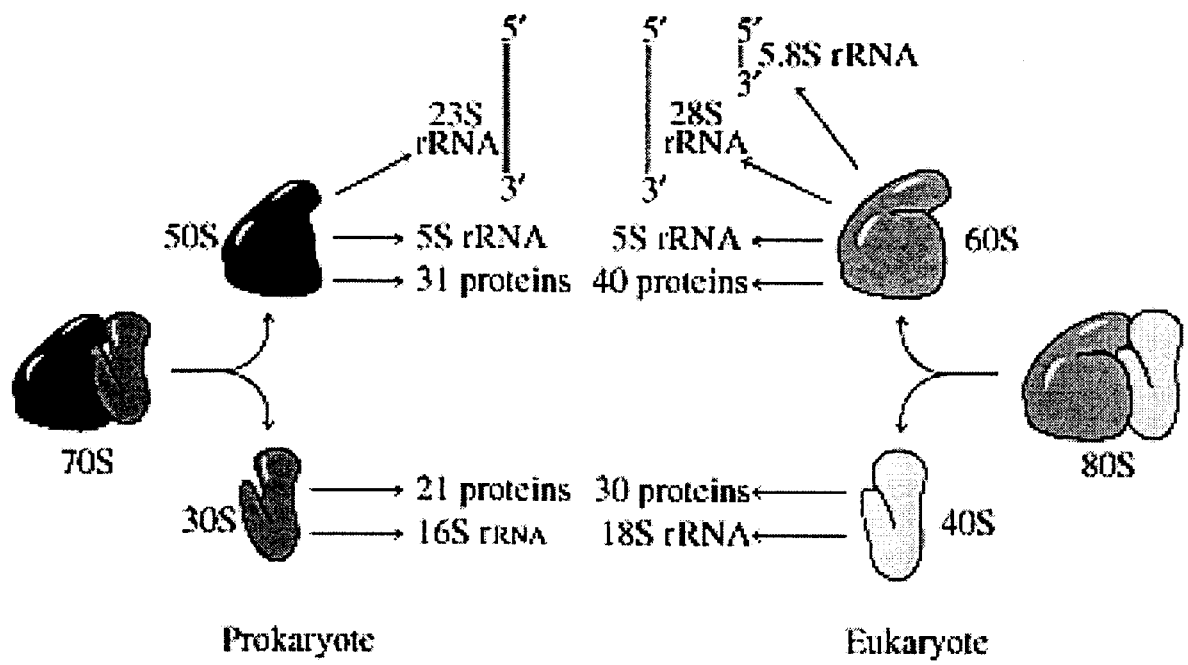
FIG. 2 illustrates a comparison of prokaryotic and eukaryotic ribosomes. Both types of ribosomes consist of two subunits, each of which contains rRNA and proteins. Peptidyl transferase activity is associated with the large subunit. The large subunits of the prokaryotic ribosome contain two molecules of rRNA: 5S and 23S. The large subunit of almost all eukaryotic ribosomes contains three molecules of rRNA: 5S, 5.8S and 28S.

Peptidyl transferase activity is an enzymatic activity that polymerizes amino acids into peptides and proteins. This activity is located on the ribosome, which is a macromolecular ribonucleoprotein-complex (RNP-complex) composed of two subunits. All ribosomes contain two subunits of unequal size. In prokaryotes, the small subunit is called the 30S subunit and the large subunit is the 50S subunit. The 30S and 50S subunits combine to form an active 70S ribosome (see, FIG. 2). In eukaryotes, the small subunit is called the 40S subunit and the larger subunit is the 60S subunit. The 40S and 60S subunits combine to form an active 80S ribosome (see, FIG. 2). In prokaryotes, the peptidyl transferase has been localized to the 50S subunit, whereas in eukaryotes, the peptidyl transferase has been localized to the 60S subunit. In the assays of the present invention, either intact ribosomes (i.e., the 70S ribosome for prokaryotes or the 80S ribosome for eukaryotes) or, alternatively, the ribosomal subunits to which the peptidyl transferase has been localized (i.e., the 50S subunit for prokaryotes or the 60S for eukaryotes) can be employed. The ribosome subunits need not be complete, so long as the components required for peptidyl trensferase activity are present.

Intact ribosomes or, alternatively, the ribosomal subunit of interest can be isolated using standard methods and procedures known to those of skill in the art. For instance, ribosomes and supernatant factors from *E. coli* can be prepared according to standard procedures described by Nishizuka, Y. & Lipmann, F., *Proc. Nat., Acad. Sci., Wash.*, 55, 212 (1967); Staehelin and Maglott, *Meth. Enzymol.*, 20, 449 (1971); and Sanchez-Madrid, et al., *Eur. J. Biochem.*, 98, 409 (1979). Typically, ribosomes extracted from microorganisms are prepared according to the following successive stages: (1) culture of the microorganism strain on a liquid or solid medium; (2) collection and lysis. of the microorganism; and (3) treatment of the lysate by repeated centrifugation at progressively higher speeds to obtain the fraction containing the ribosomes which can then be further purified. Moreover, methods for the preparation of ribosomes from eukaryotic cells vary somewhat depending on the source organism. However, procedures which can be used to isolate ribosomes derived from eukaryotic cells and which are suitable for the scale-up to the volume required for utilization in the high-throughput screening assays of the present invention are known to those of skill in the art. For instance, procedures for isolating 80S ribosomes from rabbit reticulocytes are described by, for example, Allen, E. H. and Schweet, R. S., *Journal of Biological Chemistry*, vol. 237:760–767 (1962), and Ioannou, M., et al., *Analytical Biochemistry*, vol. 247:115–122 (1997).

In the assays of the present invention, the peptidyl-tRNA analog is any compound that can become associated with the peptidyl site, i.e., P-site, of a peptidyl transferase. In a presently preferred embodiment, the peptidyl-tRNA analog is an amino acid conjugated to an oligonucleotide. Any amino acid can be conjugated to the oligonucleotide. In a presently preferred embodiment, the amino acid is a member selected from the group consisting of methionine, formyl-methionine and phenylalanine. Again, however, it will be readily apparent to those skilled in the art that additional amino acids (both natural and unnatural) can similarly be used in the assays of the present invention. Moreover, additional moieties (e.g., a label) can be added to the amino acid. The oligonucleotide to which the amino acid is conjugated can be a full length tRNA or a portion thereof. In a presently preferred embodiment, the oligonucleotide has a nucleotide sequence of a 3' end of a tRNA. Typically, the oligonucleotide is at least 3 nucleotides in length. In a preferred embodiment, the oligonucleotide has a sequence comprising 5'-CCA-3'. In another presently preferred embodiment, the oligonucleotide is at least 5 nucleotides in length and has a sequence comprising 5'-CACCA-3' or 5'-CAACCA-3'. The amino acid can be conjugated to the oligonucleotide using standard conjugation methods known to and used by those of skill in the art. Preferred peptidyl-tRNA analogs for use in the assay methods of the present invention include, but are not limited to, 5'-CCA-phenylalanine, 5'-CACCA-phenylalanine, 5'-CAACCA-methionine and 5'-CAACCA-formylmethionine.

In the assays of the present invention, the aminoacyl-tRNA analog can be any compound that resembles the structure of the 3' end of an aminoacyl-tRNA molecule and that can react with a peptidyl-tRNA analog to yield a peptidyl-aminoacyl-tRNA analog. Moreover, as described herein, the aminoacyl-tRNA analog must be capable of being detected directly (e.g., through the use of a label) or indirectly (e.g., through the use of a detection moiety that contains a label and can bind to the aminoacyl-tRNA analog). Examples of aminoacyl-tRNA analogs suitable for use in the methods of the present invention include, but are not limited to, puromycin, puromycin derivatives and other chemical entities that can function as aminoacyl-tRNA analogs in the assays of the present invention. In a preferred embodiment, puromycin is the aminoacyl-tRNA analog used in the assays of the present invention.

In the reaction mixture, the ribosome or ribosomal subunit is present at a concentration ranging from about 10 nM to about 1 $\mu$M and, more preferably, from about 50 nM to about 0.2 $\mu$M. The peptidyl-tRNA analog is present at a concentration ranging from about 1 nM to about 5 $\mu$M and, more preferably, at about 5 nM to about 100 nM. The aminoacyl-tRNA analog is present at a concentration of about 1 nM to about 200 $\mu$M and, more preferably, at a concentration ranging from about 10 $\mu$M to about 100 $\mu$M. The potential modulator of peptidyl transferase activity, if present, is present at a concentration ranging from about 1 $\mu$M to about 50 $\mu$M and, more preferably, at a concentration ranging from about 1 $\mu$M to about 10 $\mu$M.

In addition to the foregoing, the reaction mixture contains additional reaction components. Suitable reaction conditions for various peptidyl transferase, activities are known in the art (see, Monro, R. E., et al., *J. Mol. Biol.*, 25, 347–350 (1967). For instance, the reaction mixture preferably contains from about 5 to about 100 mM Tris, having a pH of about 7 to about 9, with a pH of about 8.3 being presently preferred. Moreover, the reaction mixture will contain from about 100 $\mu$M to about 500 $\mu$M KOAc and, more preferably, about 400 mM KOAc. In addition, the reaction mixture will contain from about 10 $\mu$M to about 100 $\mu$M magnesium chloride and, more preferably, about 60 $\mu$M magnesium chloride. Typically, the peptidyl transfer reaction is initiated by the addition of alcohol (e.g., methanol or ethanol), and the reaction is allowed to proceed at a temperature of about 18° C. to about 24° C. for about 30 to about 60 minutes. The alcohol is typically added at a concentration ranging from about 0% to about 40%. It will be readily apparent to those of skill in the art that substitutions can be made to the foregoing components.

C. Immobilizable Tags

In the assays of the present invention, the peptidyl-aminoacyl-tRNA analog is immobilized on a solid support. Typically, the peptidyl-tRNA analog contains an immobilizable tag. The immobilizable tag, which is attached to the peptihlyl moiety, can be any of a variety of components. In one embodiment, the immobilizable tag is immobilized, i.e., binds, directly to the solid support. In this embodiment, immobilization occurs after the peptidyl transferase reaction has occurred. For example, the peptidyl transferase reaction can be carried out in a first reaction vessel to which the immobilizable tag does not bind. After completion of the reaction, the reaction mixture is transferred to a second vessel or support to which the tag will bind, i.e., a support to which a capture moiety or tag binder is attached. In another embodiment, the peptidyl transferase reaction and the immobilization occur in a single reaction vessel, without the need to transfer the reaction mixture. Immobilization of the peptidyl-tRNA analog before the peptidyl transferase reaction can inhibit transfer of the amino acid to the aminoacyl-tRNA analog. This is avoided by using an immobilizable tag which does not bind directly to the solid support and adding to the reaction mixture, after the peptidyl transferase reaction, a capture moiety that binds to both the immobilizable tag and the solid support. In an alternative embodiment, a molecule that binds the immobilizable tag (i.e., a capture moiety or tag binder) is fixed to a solid support, and the peptidyl moiety of the peptidyl-tRNA is immobilized on the solid support as a result of the interaction between the immobilizable tag and the capture moiety.

Preferably, those of skill in the art will readily appreciate that a number of immobilizable tags and capture moieties can be used which are based upon numerous molecular interactions well described in the literature. For instance, where an immobilizable tag has a natural binder (e.g., biotin, protein A or protein G), it can be used in conjunction with an appropriate capture moiety (e.g., avidin, streptavidin, neutravidin, the Fc region of an immunoglobulin, etc.). Moreover, antibodies to molecules having natural capture moieties, such as biotin, are also widely available as appropriate capture moiety or tag binders (see, SIGMA Immunochemicals 1998 catalogue, SIGMA Chemical Co. (St. Louis Mo.)).

Similarly, any haptenic or antigenic compound can be used in combination with an appropriate antibody to form an immobilizable tag/capture moiety pair. Thousands of specific antibodies are readily available from a number of commercial sources and many additional antibodies are described in the literature (see, SIGMA's catalogue, supra). In fact, the antibody can serve as either the immobilizable tag binder or, in an indirect immobilization assay format, as the capture moiety. In one common indirect immobilization configuration, the capture moiety is a first antibody that recognizes the immobilizable tag and the solid support has bound thereto a second antibody that recognizes the first antibody. In addition to antibody-antigen interactions, receptor-ligand interactions are also appropriate as immobilizable tag and capture moiety pairs. For example, agonists and antagonists of cell membrane receptors can be used in forming immobilizable tag and capture moiety pairs. For instance, cell receptor-ligand interactions, such as transferrin, c-kit, viral receptor ligands, cytokine receptors, chemokine receptors, interleukin receptors, immunoglobulin receptors and antibodies, the cadherein family, the integrin family, the selectin family, can all be employed in the methods of the present invention (see, e.g., Pigott and Power (1993), *The Adhesion Molecule FactsBook* (Academic Press New York, and Hulme (ed.)), *Receptor Ligand Interactions: A Practical Approach*, (Rickwood and Hames (series editors) Hulme (ed.) IRL Press at Oxford Press NY). Similarly, toxins, venoms, viral epitopes, hormones (e.g., opiates, steroids, etc.), intracellular receptors (e.g., receptors which mediate the effects of various small ligands, including steroids, thyroid hormone, retinoids and vitamin D, peptides), drugs, lectins, sugars, nucleic acids (both linear and cyclic polymer configurations), oligosaccharides, proteins, phospholipids and antibodies can all interact with various cell receptors.

Synthetic polymers, such as heteropolymers, in which a known drug is covalently bound to any of the above can also form appropriate immobilizable tags or capture moieties. Such polymers include, but are not limited to, polyurethane, polyesters, polycarbonates, polyureas, polyamides, polyethyleneimines, polyarylene sulfides, polysiloxanes, polyimides, and polyacetates. Numerous other immobilizable tag/capture moiety pairs that are useful in assay systems described herein will be readily apparent to one of skill in the art upon review of this disclosure.

Specific immobilizable tag-capture moiety interactions will occur when the immobilizable tag and capture moiety bind with a $K_D$ of at least about 0.01 $\mu$M, preferably, at least about 0.001 $\mu$M or better and, most typically and preferably, 0.0001 $\mu$M or better under standard assay conditions.

Attachment of the peptidyl-tRNA analog to the various immobilizable tags is carried out using conventional methods and procedures know to and used by those of skill in the art. In one embodiment, a linker is added to the peptidyl-tRNA analog and attachment to the immobilizable tag is carried out through the use of the linker. Suitable linkers include, but are not limited to, proteins, carbohydrates, lipids, peptides, polyester, nucleic acids and synthetic polymers. Common linkers include polypeptide sequences, such as poly-gly sequences of between about 5 and 200 amino acids. In some embodiments, proline residues are incorporated into the linker to prevent the formation of significant secondary structural elements by the linker. Flexible linkers suitable for use in the present invention are known to persons of skill in the art. For example, poly(ethylene glycol) linkers are available from Shearwater Polymers, Inc. (Huntsville, Ala.). These linkers optionally have amide linkages, sulfhydryl linkages, or heterobifunctional linkages. The immobilizable tag should be attached in a manner that does not interfere with the ability of the peptidyl-tRNA analog to act as a substrate for the peptidyl transferase.

Capture moieties or tag binders are fixed to solid substrates using any of a variety of methods currently available. Solid substrates are commonly derivatized or functionalized by exposing all or a portion of the substrate to a chemical reagent that fixes a chemical group to the surface which is reactive with a portion of the capture moiety. For example, groups that are suitable for attachment to a longer chain portion include, but are not limited to, amine, hydroxyl, thiol and carboxyl groups. Aminoalkylsilanes and hydroxyalkylsilanes can be used to functionalized a variety of surfaces, such as a glass surface. The construction of such solid phase biopolymer arrays is well described in the literature (see, e.g., Merrifield, *J. Am. Chem. Soc.*, 85:2149–2154 (1963) (describing solid phase synthesis of, e.g., peptides); Geysen, et al., *J. Immun. Meth.*, 102:259–274 (1987) (describing synthesis of solid phase components on pins); Frank and Doring, *Tetrahedron*, 44:6031–6040 (1988) (describing synthesis of various peptide sequences on cellulose disks); Fodor, et al., *Science*, 251:767–777 (1991); Sheldon, et al., *Clinical Chemistry* 39(4):718–719 (1993); and Kozal, et al., *Nature Medicine*, 2(7):753–759 (1996) (all describing arrays of biopolymers fixed to solid substrates). Non-chemical approaches for fixing capture moieties to substrates include commonly methods, such as heat, cross-linking by UV radiation, and the like.

In the assays of the present invention, the tagged peptidyl-tRNA analog is immobilized on or bound to a solid support or solid phase. Typically, the solid support is a matrix of material in a substantially fixed arrangement (i.e., an insoluble polymeric material, inorganic or organic matrix, gel, aggregate, precipitate or resin). Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Preferred solid supports in accordance with the present invention include, but are not limited to, the following: cellulose, agarose, dextran, polyacrylate, polyacrylamide, polystyrene, polyvinyl chloride, or their derivatives, chitin, sepharose, oxirane substituted acrylic beads, starch, oxidized starch (i.e., polymeric dialdehyde), collagen, keratin, elastin, bovine hide powder, bacterial cell wall peptidoglycan or fragments thereof, diazotized paper, nylon, polyethylene terephthalates, polycarbonates, metallic particles and controlled pore glass. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham, Mass.), Ciba Coming (Medfield, Mass.), Bangs Laboratories (Carmel, Ind.), and BioQuest, Inc. (Atkinson, N.H.). Of these, certain solid supports are presently preferred, namely, cellulose and cellulose derivatives (e.g., nitrocellulose), agarose, dextran, polyacrylate, polyacrylamide, polystyrene, polyvinyl chloride and glass. Even more preferred for use as a solid support are nitrocellulose, polystyrene and polyvinyl chloride. Polystyrene and polyvinyl chloride are normally used as microtiter plates, while nitrocellulose is normally used in sheets.

Once the tagged peptidyl-tRNA analog and, if present, the covalently linked aminoacyl-tRNA analog are fixed to the solid support, the support is washed to remove non-immobilized components. Wash conditions are selected so that the immobilizable tag remains bound to any capture moieties, and any covalently bound aminoacyl-tRNA analog remains bound to the peptidyl moiety of the peptidyl-tRNA analog. Preferably, a high salt wash is used, e.g., about 0.2 to 2 M NaCl or KCl. Suitable wash solutions include, for example, TBS-T buffer containing 1 M NaCl (see, Examples). One or more washes can be employed. In preferred embodiments, washes are repeated until a signal to noise ratio of 2×–10× (or higher) is achieved, i.e., until at least about 50–90% of the unattached aminoacyl-tRNA analog is removed from the solid support, and often until at least 90–95% is removed. The determination of how much aminoacyl-tRNA analog remains can be done by performing a calibration of the assay, i.e., by performing the peptidyl transferase assay in the absence of a modulator and then repeatedly washing the solid support to determine the amount of the aminoacyl-tRNA analog bound to the support through the peptidyl moiety of the peptidyl-tRNA analog, and the number of washes required to remove unbound aminoacyl-tRNA.

D. Labeling Strategies

As discussed above, the aminoacyl-tRNA analog must be capable of being detected directly or indirectly. The detectable labels used in the present invention can be primary labels (where the label comprises an element that is detected directly or that produces a directly detectable element) or, alternatively, they can be secondary labels (where the detected label binds to a primary label, e.g., as is commonly used in immunological labeling). An introduction to labels, labeling procedures and detection of labels is found in Polak and Van Noorden, Introduction to Immunocytochemistry (2nd ed. Springer Verlag, NY (1997)); and in Haugland, Handbook of Fluorescent Probes and Research Chemicals, a combined handbook and catalogue Published by Molecular Probes, Inc. (Eugene, Oreg. (1996)). Primary and secondary labels can include undetected elements as well as detected elements. Primary and secondary labels useful in the present invention include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3H$, $^{125}I$, $^{35}S$, $^{14}C$, $^{32}P$, $^{33}P$, etc.; enzymes, such as horse radish peroxidase, alkaline phosphatase, etc.; spectral calorimetric labels, such as colloidal gold or colored glass or plastic beads, such as polystyrene, polypropylene, latex, etc. The label can be coupled directly or indirectly to a component of the detection assay (e.g., the aminoacyl-tRNA analog) using methods well known in the art. For example, one can detect the aminoacyl-tRNA analog by contacting the analog with a detection moiety that comprises a label and binds to the analog. As indicated above, a wide variety of labels can be used, with the choice of label depending on sensitivity required, ease of conjugation with the aminoacyl-tRNA analog, stability requirements, and available instrumentation and disposal provisions.

Preferred labels include those that use: 1) chemiluminescence (using horseradish peroxidase and/or alkaline phosphatase with substrates that produce photons as breakdown products as described above), with kits being available from, for example, Molecular Probes, Amersham, Boehringer-Mannheim, and Life Technologies/Gibco BRL; 2) color production (using both horseradish peroxidase and/or alkaline phosphatase with substrates that produce a colored precipitate), with kits being available from Life Technologies/Gibco BRL, and Boehringer-Mannheim; 3) hemifluorescence (using, for example, alkaline phosphatase and the substrate AttoPhos [Amersham] or other substrates that produce fluorescent products), 4) fluorescence (e.g., using Cy-5 [Amersham]), fluorescein, and other fluorescent tags); and 5) radioactivity. Other methods for labeling and detection will be readily apparent to one skilled in the art.

Preferred enzymes that can be conjugated to the detection moieties of the invention include, but are not limited to, β-galactosidase, luciferase, horse radish peroxidase and alkaline phosphatase. The chemiluminescent substrate for luciferase: is luciferin. One example of a chemiluminescent substrate for β-galactosidase is 4-methylumbelliferyl-β-D-galactoside. Examples of alkaline phosphatase substrates include p-nitrophenyl phosphate (pNPP), which is detected using a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3, 2'-adamantane], which is detected using a luminometer. Examples of horseradish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected using a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

Most typically, peptidyl transferase activity is measured by quantitating the amount of label fixed to the solid support by binding of the detection moieties. Typically, presence of a modulator during incubation will increase or decrease the amount of label fixed to the solid support relative to a control incubation which does not comprise the modulator, or as compared to a baseline established for a particular reacti on type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems that are widely available.

In general, a detector which monitors a particular probe or probe combination is used to detect the label. Typical detectors include, but are not limited to, spectrophotometers, phototubes and photodiodes, microscopes, scintillation counters, cameras, film and the like, as well as combinations thereof. Examples of suitable detectors are widely available from a variety of commercial sources known to persons of skill.

E. Modulators

The invention also provides methods of identifying compounds that modulate peptidyl transferase activity. Essentially any chemical compound can be used as a potential activity modulator in the assays of the invention, although most often compounds that can be dissolved in aqueous or organic (especially DMSO-based) solutions are used. The assays are designed to screen large chemical libraries by automating the assay steps and providing compounds from any convenient source to assay, which are typically run in parallel (e.g., in microtiter formats on microtiter plates in robotic assays). It will be appreciated by those of skill in the art that there are many commercial suppliers of chemical compounds, including Sigma Chemical Co. (St. Louis, Mo.), Aldrich Chemical Co. (St. Louis, Mo.), Sigma-Aldrich (St. Louis, Mo.), Fluka Chemika-Biochemica Analytika (Buchs Switzerland), and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those, library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487–493 (1991) and Houghton, et al., *Nature*, 354:84–88 (1991)). Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA*, 90:6909–6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.*, 114:9217–9218 (1992)); analogous organic syntheses of small compound libraries (Chen, et al., *J. Amer. Chem. Soc.*, 116:2661 (1994)); oligocarbamates (Cho, et al., *Science*, 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology*, 14(3):309–314 (1996) and PCT/US96/10287); carbohydrate libraries (see, e.g., Liang, et al., *Science*, 274:1520–1522 (1996) and U.S. Pat. No. 5,593,853); small organic molecule libraries (see, e.g., benzodiazepines, Baum C&E News, Jan. 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

As noted, the invention provides in vitro assays for peptidyl transferase activity in a high-throughput format. Control reactions that measure peptidyl transferase activity in a reaction that does not include a peptidyl transferase activity modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions, which do not include a modulator, provide a background level of binding activity.

In some assays it will be desirable to have positive controls to ensure that the components of the assays are working properly. At least two types of positive controls are appropriate. First, a known activator of peptidyl transferase can be incubated with one sample of the assay, and the resulting increase in peptidyl transferase activity determined according to the methods herein. Second, a known inhibitor of peptidyl transferase can be added, and the resulting decrease peptidyl transferase activity similarly detected. It will be appreciated that modulators can also be combined with peptidyl transferase activators or inhibitors to find modulators which inhibit peptidyl transferase activation or repression that is otherwise caused by the presence of the known peptidyl transferase modulator.

In the high throughput assays of the invention, it is possible to screen up to several thousand different modulators in a single day. In particular, each well of a microtiter plate can be used to run a separate assay against a selected potential modulator, or if concentration or incubation time effects are to be observed, every 5–10 wells can test a single modulator. Thus, a single standard microtiter plate can assay about 100 (96) modulators. If 1536 well plates are used, then a single plate can easily assay from about 100–about 1500 different compounds. It is possible to assay many different plates per day; assay screens for up to about 6,000–20,000, and even up to about 100,000–1,000,000 different compounds is possible using the integrated systems of the invention.

F. Compositions, Kits and Integrated Systems

The invention provides compositions, kits and integrated systems for practicing the assays described herein. For example, an assay composition having a peptidyl-tRNA analog, an aminoacyl-tRNA analog, an immobilizable tag bound to the peptidyl-tRNA analog and a label bound to the aminoacyl-tRNA analog is provided by the present invention. Additional assay components as described above are also provided. For instance, a solid support or substrate to which the tagged peptidyl-tRNA analog can be bound can also be included. Such solid supports include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The invention also provides kits for practicing the peptidyl transferase screening assays described above. The kits can include any of the compositions noted above, and optionally further include additional components such as instructions to practice a high-throughput method of screening for a peptidyl transferase activity modulator, one or more containers or compartments (e.g., to hold peptidyl-tRNA analogs, uninoacyl-tRNA analogs, modulators, or the like), a control activity modulator, a robotic armature for mixing kit components, and the like.

The invention also provides integrated systems for high throughput screening of potential modulators for peptidyl transferase activity. Such systems typically include a robotic armature which transfers fluid from a source to a destination, a controller which controls the robotic armature, a label detector, a data storage unit which records label detection, and an assay component such as a microtiter dish comprising a well having a capture moiety for a peptidyl-tRNA analog affixed to the well.

A number of well-known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art.

Any of the assays for compounds that modulate peptidyl transferase activity, as described herein, are amenable to high throughput screening. High throughput screening systems are commercially available (see, e.g., Zymark Corp. (Hopkinton, Mass.); Air Technical Industries (Mentor, Ohio); Beckman Instruments, Inc. (Fullerton, Calif.); Precision Systems, Inc., (Natick, Mass.), etc.). Such systems typically automate entire procedures including all sample and reagent pipetting, liquid dispensing, timed incubations, and final readings of the microplate in detector(s) appropriate for the assay. These configurable systems provide high-throughput and rapid start up as well as a high degree of flexibility and customization. The manufacturers of such systems provide detailed protocols for the various high throughput systems.

Optical images viewed (and, optionally, recorded) by a camera or other recording device (e.g., a photodiode and data storage device) are optionally further processed in any of the embodiments described herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

G. Exemplar In Vitro Formats For Assaying For Peptidyl Transferase Activity

The assays of the present invention are further illustrated by consideration of the attached FIGS. 3–6. These assays are provided by way of illustration and not by way of limitation; one of skill will recognize a variety of substitutions that can be made upon complete review of this disclosure.

Figure 3:
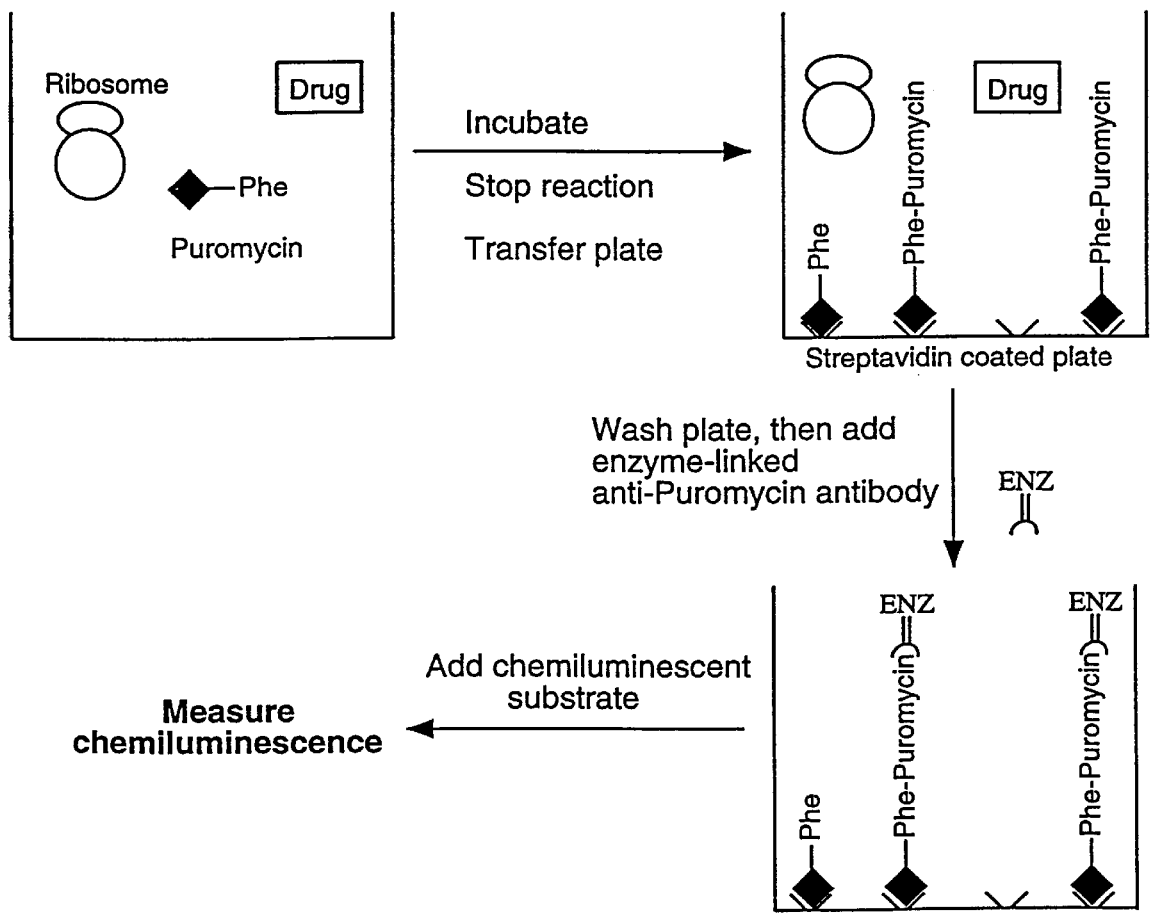
FIG. 3 illustrates one embodiment of the peptidyl transferase HTS assay of the present invention. In this assay, the aminoacyl-tRNA analog, i.e., the A-site substrate, is puromycin and the peptidyl-tRNA analog, i.e., the P-site substrate, is 5'-CACCA-(N)-biotin-phenylalanine or 5'-CCA-(N)-biotin-phenylalanine.

Format 1:

FIG. 3 illustrates a preferred exemplar embodiment of the peptidyl transferase HTS assay of the present invention. In this assay, the aminoacyl-tRNA analog, i.e., the A-site substrate, is puromycin and the peptidyl-tRNA analog is 5'-CACCA-(N)-biotin-phenylalanine or 5'-CCA-(N)-biotin-phenylalanine. If peptidyl transferase is present, the reaction product is biotin-phenylalanine-puromycin. The reaction product is captured via streptavidin-coated, secondary (transfer) plate and detected using a primary antibody (or antisera) with avidity and specificity for puromycin, in combination with an enzyme-linked secondary antibody specific for recognition of the primary antibody. The read-out is chemiluminescence resulting from conversion of a substrate specific for the secondary antibody-enzyme conjugate to a chemiluminescent product.

Figure 4:
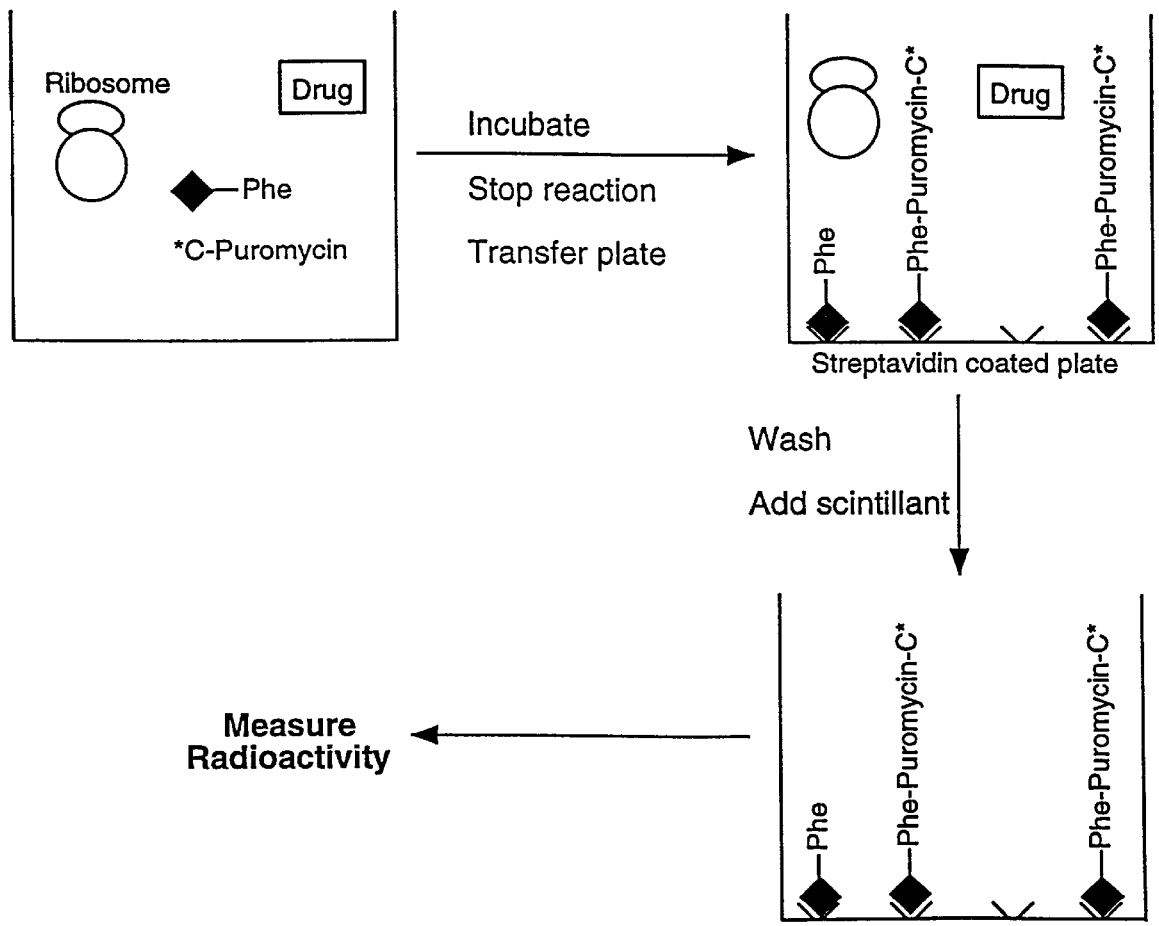
FIG. 4 illustrates another embodiment of the peptidyl transferase HTS assay of the present invention. In this assay, the aminoacyl-tRNA analog, i.e., tide A-site substrate, is 5'-$^{32}$P-C-puromycin and the peptidyl-tRNA analog, i.e., the P-site substrate, is 5'-CACCA-(N)-biotin-phenylalanine or 5'-CCA-(N)-biotin-phenylalanine.

Format 2:

FIG. 4 illustrates another exemplar embodiment of the peptidyl transferase HTS assay of the present invention. In this assay, the peptidyl-tRNA analog is 5'-CACCA-(N)-biotin-phenylalanine and the aminoacyl-tRNA analog, i.e., the A-site substrate, is radiolabeled puromycin (e.g., $^3$H-puromycin) or a derivative thereof (e.g., $^{32}$P-C-puromycin). For the latter, if peptidyl transferase is present, the reaction product is biotin-phenylalanine-puromycin-C-$^{32}$P. The reaction product is captured is streptavidin-coated, secondary (transfer) plate and detected using radioisotopic detection ($^{32}$P). The read-out is carried out using a scintillation counter.

Figure 5:
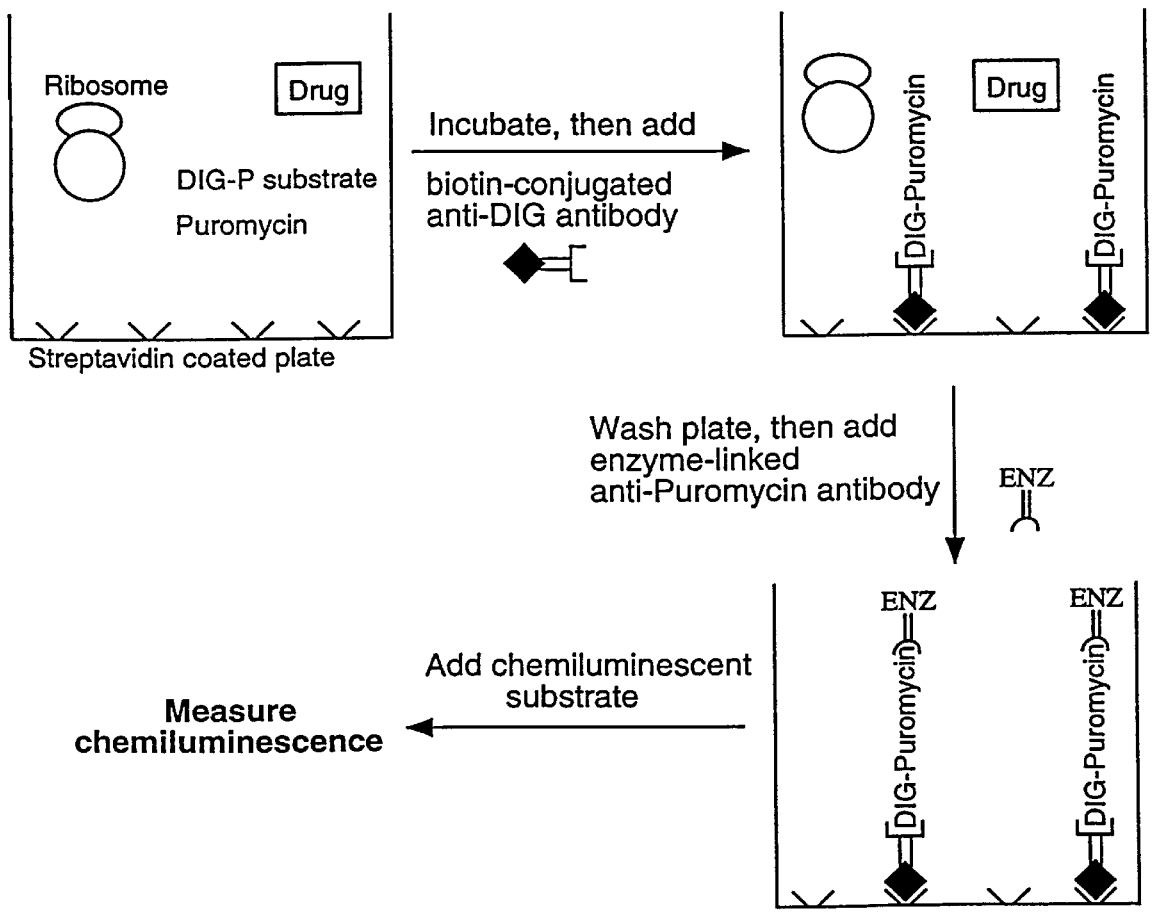
FIG. 5 illustrates yet another embodiment of the peptidyl transferase HTS assay of the present invention. In this assay, the aminoacyl-tRNA analog, i.e., the A-site substrate, is puromycin and the peptidyl-tRNA analog, i.e., the P-site substrate, is 5'-CACCA-(N)-digoxigenin-phenylalanine or 5'-CCA-(N)-digoxigenin-phenylalanine.

Format 3:

FIG. 5 illustrates yet another exemplar embodiment of the peptidyl transferase HTS assay of the present invention. In this assay, the aminoacyl-tRNA analog, i.e., the A-site substrate, is puromycin and the peptidyl-tRNA analog is 5'-CACCA-(N)-digoxigenin-phenylalanine or 5'-CCA-(N)-digoxigenin-phenylalanine. If peptidyl transferase is present, the reaction product is digoxigenin-phenylalanine-puromycin. The reaction product is captured via addition of biotin-conjugated antidigoxigenin antibody using a primary streptavidin-coated plate. Detection is carried out using a primary antibody (or antisera) with avidity and specificity for puromycin, in combination with an enzyme-linked secondary antibody specific for recognition of the primary antibody. The read-out is carried out using chemiluminescence resulting from conversion of a substrate specific for the secondary antibody-enzyme conjugate to a chemiluminescent product.

Figure 6:
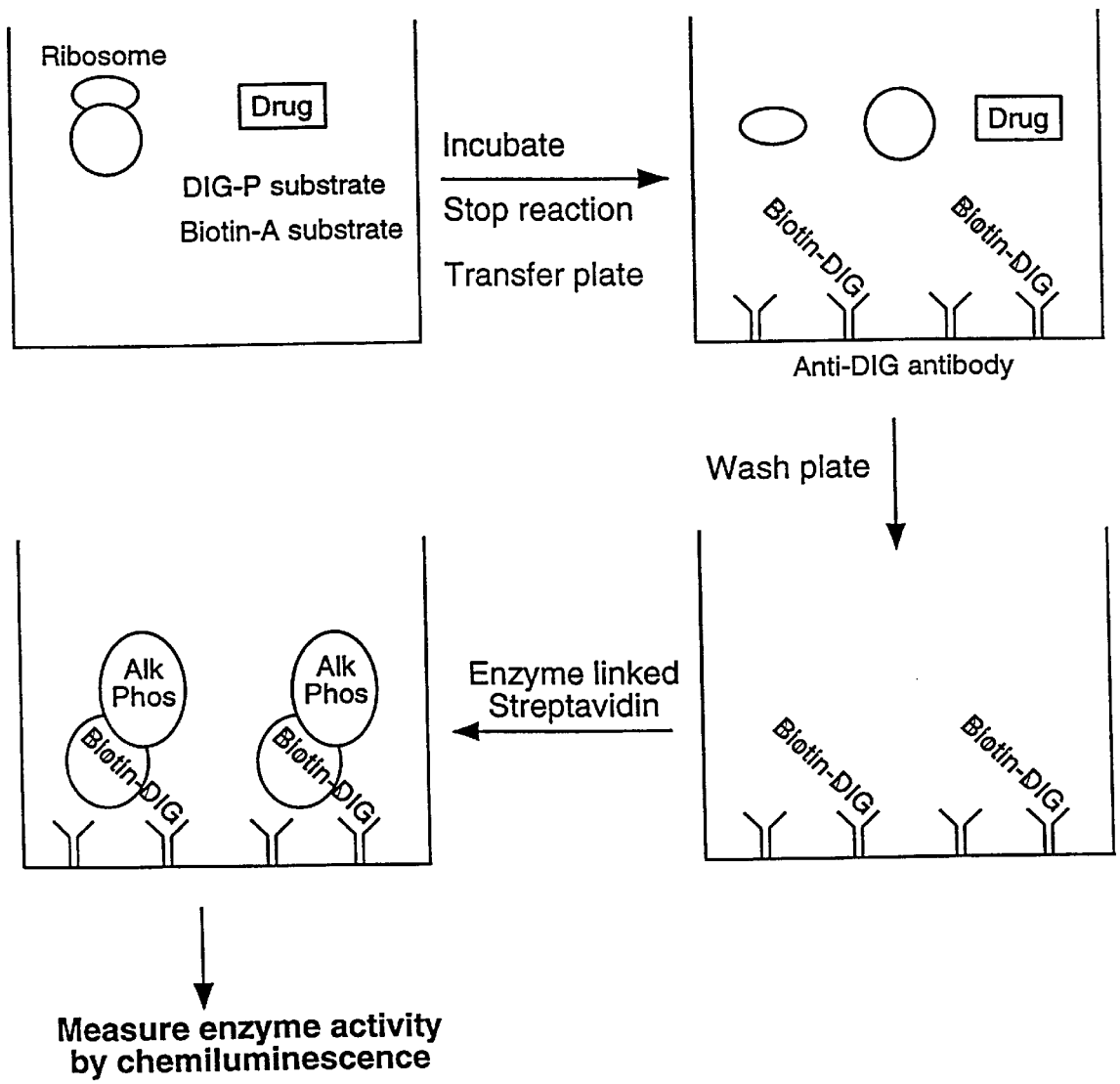
FIG. 6 illustrates still another embodiment of the peptidyl transferase HTS assay of the present invention. In this assay, the aminoacyl-tRNA analog, i.e., the A-site substrate, is 5'-dT-biotin-C-puromycin and the peptidyl-tRNA analog, i.e., the P-site substrate, is 5'-CACCA-(N)-digoxigenin-phenylalanine or 5'-CCA-(N)-digoxigenin-phenylalanine.

Format 4:

FIG. 6 illustrates still another exemplar embodiment of the peptidyl transferase HTS assay of the present invention. In this assay, the aminoacyl-tRNA analog, i.e., the A-site substrate, is 5'-dT-biotin-C-puromycin and the peptidyl-tRNA analog is 5'-CACCA-(N)-digoxigenin-phenylalanine or 5'-CCA-(N)-digoxigenin-phenylalanine. If peptidyl transferase is present, the reaction product is digoxigenin-phenylalanine-puromycin-biotin-dT. The reaction product is carried out via secondary plate coated with antidigoxigenin antibody and detection is by an enzyme-linked avidin (or streptavidin). The read-out is carried out by chemiluminescence resulting from conversion of a substrate specific for the secondary enzyme-linked avidin conjugate to a chemiluminescent product.

The invention will be described in greater detail by way of specific examples. The following examples are offered for illustrative purposes, and are not. intended to limit the invention in any manner. Those of skill in the art will readily recognize a variety of noncritical parameters that can be changed or modified to yield essentially the same results.

EXAMPLES

A. Format 1:

70S ribosomes were prepared from *Escherichia coli* MRE600 using methods that are essentially the same as those described in Staehelin, T. and Maglott, D. R., (1971), *Methods in Enzymology*, 20:449, Traub, P., et al., (1981) Chapter 49 from *RNA and Protein Synthesis* (Academic Press, Inc.), pp. 521–538, and Spedding, G., (1990) Chapter 1 from *Ribosomes and Protein Synthesis: A Practical Approach*, (Spedding, Cr. (ed.), Oxford Univ. Press, Oxford), pp. 1–29; from *Bacillus subtilis* 168 using methods that are essentially the same as those described by Fahnestock, S., et al., (1974) *Methods in Enzymology*, 30:554–562; and from *Staphylococcus aureus* using methods that are essentially the same as those described by Martin, S. E. and Iandolo, J. J., (1975) *Journal of Bacteriology*, 122:1136–1143. The biotin-labeled P-site substrate employed was 5'-CACCA-(N)-biotin-phenylalanine which was prepared essentially as described in Moazed and Noller (1991) using the following steps: (i) in vitro preparation of phenylalanine-tRNA$^{phe}$, (ii) reaction of this product with biotinyl-$\epsilon$-aminocaproic acid-N-hydroxysuccinimide to form N-biotinyl-phenylalanine-tRNA$^{phe}$, (iii) cleavage of the latter with ribonuclease T1, and (iv) purification of the 5'-rCrArCrCrA-O3'-(N-Biotinyl-Phe) molecule. Puromycin (the A-site substrate used in the reaction shown) and the antibiotics used as 'control drugs' were obtained from Sigma; while the streptavidin-coated plates were obtained from Pierce.

In the examples shown, chemiluminescent detection of plate-immobilized puromycin containing molecules was effected by utilization of (i) a primary IgG antibody raised in rabbits against which is cross-reactive with puromycin, (ii) a mouse anti-rabbit IgG antibody conjugated to horse radish peroxidase (HRP), and (iii) addition of an HRP substrate which yields a chemiluminescent product upon reaction with HRP.

FIGS. 7a–7e illustrate representative data obtained from assays run in accordance with the assay format shown in FIG. 3 and using reagents and methodologies as described above. For these reactions, the following reagents (where present) and reaction conditions were employed in 100 $\mu$l reactions:

P-site substrate: 10–100 pmol of 5'-CACCA-(N)-biotin-phenylalanine
A-site substrate: 20 nmol Puromycin
Ribosomes: 20 pmol of 70S preparation from *E.coli* MRE600
Reaction buffer: 50 mM Tris pH 8.3, 0.4M KOAc, 60 mM MgCl$_2$, 10% DMSO, 33% MeOH
Reaction condition: 30 mins at room temperature (~20° C.)
Wash Buffer: TBS-T=Tris-buffered saline (Biorad) containing 0.05% Tween-20.
Primary antibody: 1:5,000 dilution of rabbit anti-puromycin antibody
Secondary antibody: 1:10,000 dilution of a rabbit anti-mouse IgG antibody conjugated to horseradish peroxidase (Amersham).
HRP substrate: Supersignal (Pierce).
Drugs: In 7c, all inhibitors were present at 100 $\mu$M In 7d and 7e, chloramphenicol or virginiamycin M$_1$ was included at the concentrations indicated in the figure.
Detection: Chemiluminometer was employed and the data recorded as relative light intensity units (RLU's).

Reactions were set up in 96-well, plastic microtitre plates and incubated for 30 minutes at room temperature. Thereafter, the reactions were transferred to streptavidin-coated microtitre plates (commercially available from Pierce) and incubated for a further 30 minutes at room temperature. The reaction wells were then emptied of fluid and washed three times with 200 $\mu$l of a wash buffer which comprised 1 M NaCl, 0.05% Tween-20, 20 mM Tris.HCl (pH 7.5), and the reaction wells were then rinsed with 200 $\mu$l of TBS-T. 100 $\mu$l of a 1:5,000 dilution of the primary antibody (in TBS plus 1% BSA) was then added and the plate incubated for an additional 30 minutes at room temperature. The reaction wells were then emptied of fluid and washed three times with 200 $\mu$l of TBS-T. 100 $\mu$l of a 1:10,000 dilution of the secondary was then added and the plate incubated for an additional 30 minutes at room temperature. The reaction wells were then emptied of fluid and washed three times with 200 $\mu$l of TBS-T. Detection of HRP-conjugated, secondary antibody was then effected by addition of the Supersignal HRP substrate reagent (commercially available from Pierce) and reading in a chemiluminometer.

Figure 7A:
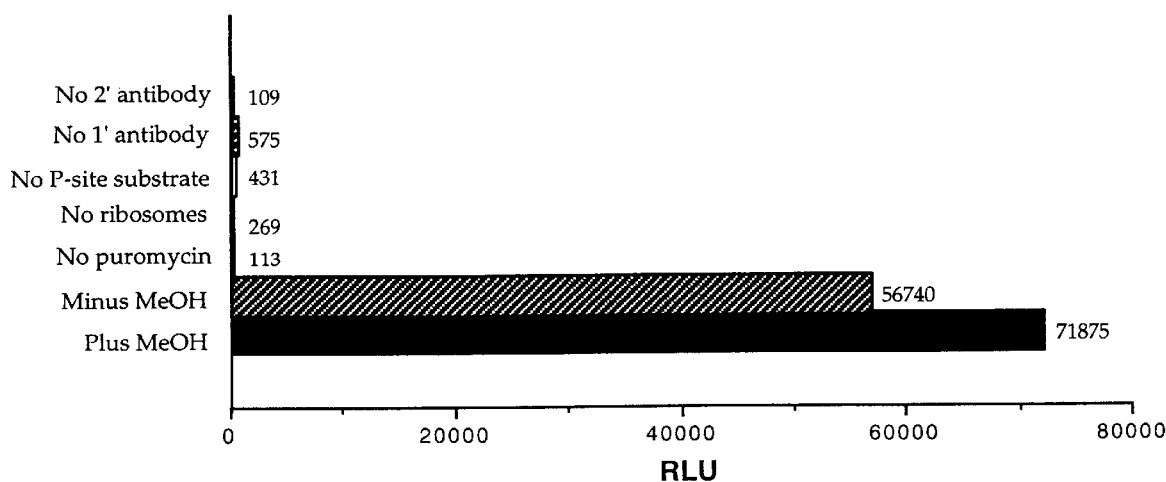
Figure 7B:
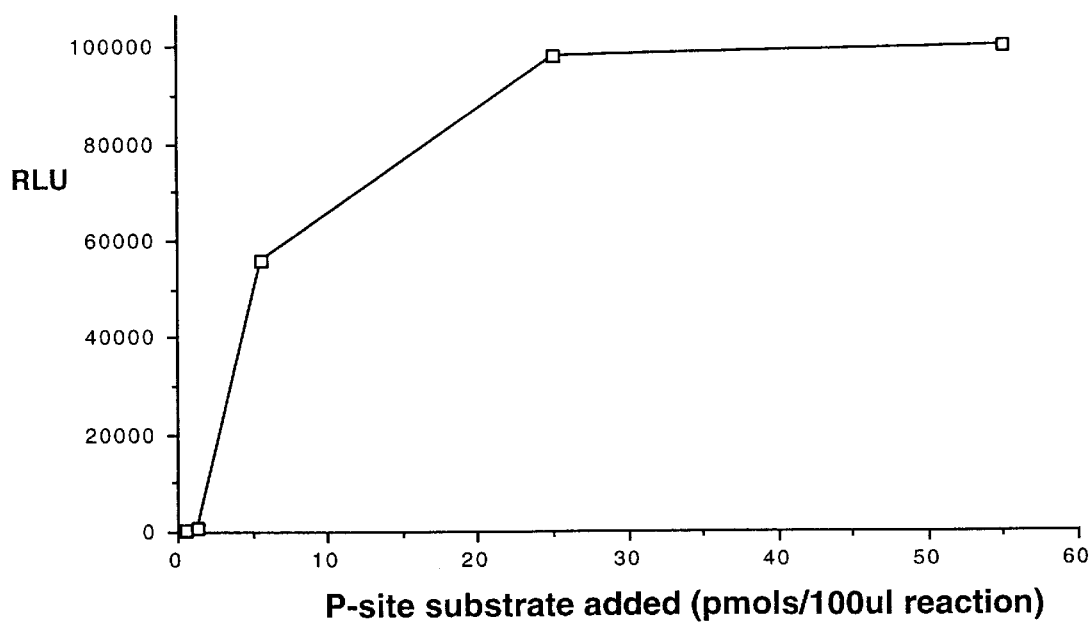

FIGS. 7a–7d demonstrate the efficacy of the assay illustrated in FIG. 3 and its ability to identify novel inhibitors of the peptidyl transferase activity. FIG. 7a demonstrates the dependence of the assay on addition of each of the major components, and the relative insensitivity of the assay to the inclusion of 33% (vol:vol) methanol. FIG. 7b demonstrates the dependence of the assay on the concentration of the P-site substrate added to the reaction. FIG. 7c demonstrates the sensitivity of the assay to a range of known inhibitors of the peptidyl transferase reaction, and the insensitivity of the assay to other antibiotics which inhibit protein translation via effects on other components of the translational machinery. FIGS. 7d and 7e show dose-responses obtained with two peptidyl transferase inhibitors, i.e., chloramphenicol and virginiamycin M$_1$, respectively.

B. Format 2:

Ribosomes, the P-site substrate (5'-CACCA-(N)-biotin-phenylalanine) and other reaction reagents were prepared and/or used as described for the reactions carried out in Format 1 above. In the example shown in FIG. 8, a $^{32}$P-labeled C-Puromycin was used as the A-site substrate and was prepared as described by Green et al. (1998). For these reactions, the following reagents (where present) and reaction conditions were employed in 100 $\mu$l reactions:

P-site substrate: 100 pmol of 5'-CACCA-(N)-biotin-phenylalanine.
A-site substrate: 1–10 pmol of $^{32}$P-labeled C-Puromycin.
Ribosomes: 20 pmol of 70S preparation from *E. coli* MRE600.
Reaction buffer: 50 mM Tris pH 8.3, 0.4 M KOAc, 60 mM MgCl$_2$, 10% DMSO, 33% MeOH.
Reaction condition: 30 mins. at room temperature (~20° C.).
Drugs: Carbomycin was present at 100 $\mu$M.
Detection: Scintillation counting and data recorded as counts per minute (CPM's)

Figure 8A:
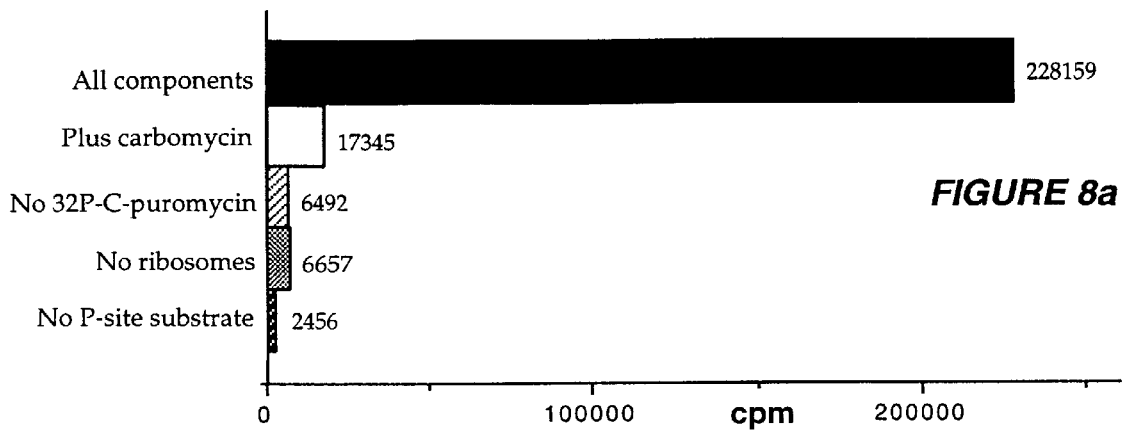
FIGS. 8a–8c demonstrate the efficacy of the assay illustrated in FIG. 4 and its ability to identify novel inhibitors of the peptidyl transferase activity.
Figure 8B:
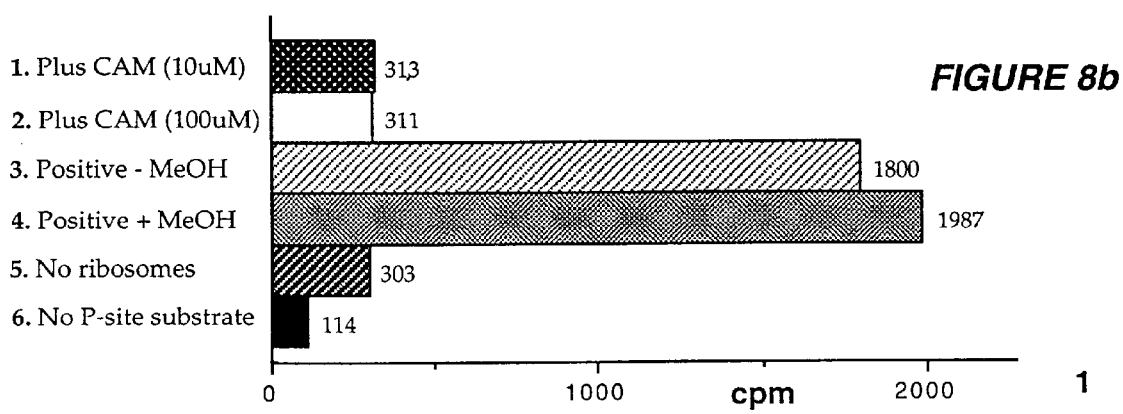
Figure 8C:
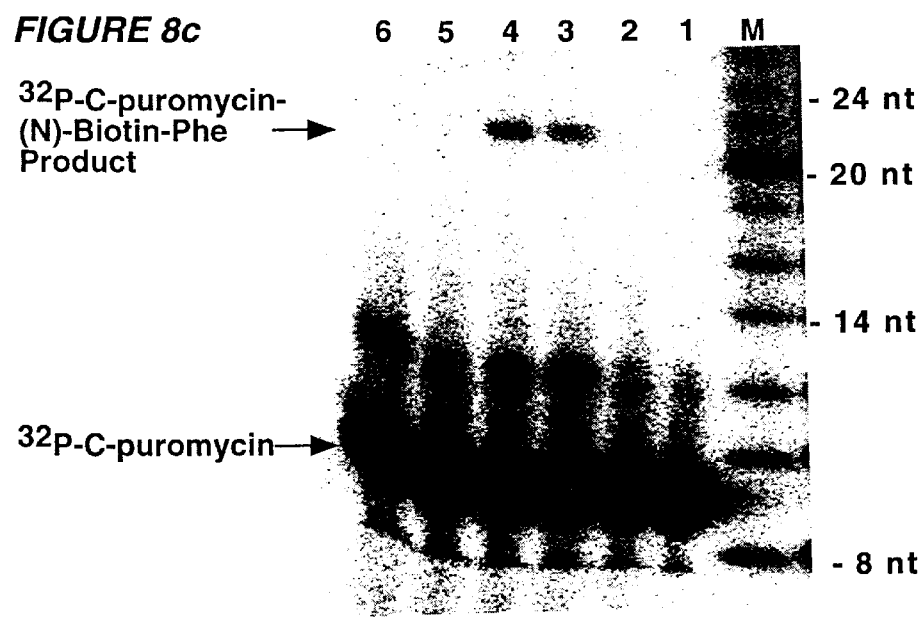

FIGS. 8a–8c demonstrate the efficacy of the assay illustrated in FIG. 4 and its ability to identify novel inhibitors of the peptidyl transferase activity. FIGS. 8a and 8b demonstrate the dependence of the assay on the addition of each of the major components, and the sensitivity of the assay to the inclusion of known peptidyl transferase inhibitors (e.g., chloramphenicol and virginiamycin M1). Verification of the integrity of the peptidyl transferase reaction product ($^{32}$P-C-puromycin-(N)-biotin-phenylalanine) formed during the reactions shown in FIG. 8b is demonstrated in the data shown in FIG. 8c. The reactions illustrated in FIGS. 8b and 8c were set up as described above; however, after the initial reaction of 30 minutes at room temperature, an aliquot of each was removed and resolved on a 20% polyacrylamide gel (Green, R., et al., (1998), "Localization of a conserved loop of 23S rRNA at the peptidyl transferase A site," *Science* (in press)).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for determining peptidyl transferase activity, the method comprising:
    incubating a reaction mixture comprising a peptidlyl transferase, a peptidyl-tRNA analog which comprises a peptidyl moiety to which is attached an immobilizable tag, and an aminoacyl-tRNA analog under conditions suitable for transfer of the peptidyl moiety to said aminoacyl-tRNA analog;
    binding the immobilizable tag of the peptidyl moiety of said peptidyl-tRNA analog to a solid support; and
    detecting the presence of said aminoacyl-tRNA analog on said solid support as an indication of peptidyl transferase activity.

2. The method in accordance with claim 1 wherein said peptidyl transferase comprises a 23S rRNA.

3. The method in accordance with claim 1 wherein said peptidyl transferase comprises a 23S rRNA associated with a subset of proteins so as to reconstitute functional peptidyl transferase activity.

4. The method in accordance with claim 2 wherein said 23S rRNA comprises a ribosome.

5. The method in accordance with claim 4 wherein said ribosome is intact.

6. The method in accordance with claim 4 wherein said ribosome is a prokaryotic ribosome.

7. The method in accordance with claim 1 wherein said peptidyl transferase comprises a 28S rRNA.

8. The method in accordance with claim 1 wherein said peptidyl transferase comprises a 28S rRNA associated with a subset of proteins so as to reconstitute functional peptidyl transferase activity.

9. The method in accordance with claim 7 wherein said 28S rRNA comprises a ribosome.

10. The method in accordance with claim 9 wherein said ribosome is intact.

11. The method in accordance with claim 9 wherein said ribosome is an eukaryotic ribosome.

12. The method in accordance with claim 1 further comprising a potential modulator of peptidyl transferase activity.

13. The method in accordance with claim 1 further comprising transferring said reaction mixture to said solid support to which said immobilizable tag binds directly.

14. The method in accordance with claim 1 wherein said immobilizable tag binds to said solid support indirectly.

15. The method in accordance with claim 14 wherein said immobilizable tag is contacted with a capture moiety that binds to said solid support.

16. The method in accordance with claim 1 wherein said aminoacyl-tRNA analog is directly detected.

17. The method in accordance with claim 1 wherein said aminoacyl-tRNA analog is indirectly detected.

18. The method in accordance with claim 17 wherein said aminoacyl-tRNA analog is contacted with a detection moiety that comprises a detectable label.

19. The method in accordance with claim 18 wherein said detection moiety is an antibody against said aminoacyl-tRNA analog.

20. The method in accordance with claim 1 wherein said peptidyl-tRNA analog is an amino acid conjugated to an oligonucleotide having a nucleotide sequence of a 3' end of a tRNA.

21. The method in accordance with claim 20 wherein said oligonucleotide is at least about 3 nucleotides in length.

22. The method in accordance with claim 20 wherein said oligonucleotide has a sequence comprising 5'-CCA-3'.

23. The method in accordance with claim 20 wherein said oligonucleotide is at least about 5 nucleotides in length.

24. The method in accordance with claim 20 wherein said oligonucleotide has a sequence comprising 5'-CACCA-3'.

25. The method in accordance with claim 20 wherein said amino acid is a member selected from the group consisting of naturally occurring amino acids and other amino acids and amino acid analogs that can function as the amino acid component of said peptidyl-tRNA analog.

26. The method in accordance with claim 20 wherein said oligonucleotide has a sequence comprising 5'-CAACCA-3'.

27. The method in accordance with claim 20 wherein said amino acid is selected from the group consisting of phenylalanine, methionine and formylmethionine.

28. The method in accordance with claim 1 wherein said aminoacyl-tRNA analog is a member selected from the group consisting of puromycin, puromycin derivative and other chemical entities that function as aminoacyl-tRNA analogs.

29. A method for identifying a modulator of peptidyl transferase activity, the method comprising:
    incubating a reaction mixture comprising a peptidyl transferase, a peptidyl-tRNA analog which comprises a peptidyl moiety to which is attached an immobilizable tag, a aminoacyl-tRNA analog and a modulator under conditions suitable for transfer of the peptidyl moiety to said aminoacyl-tRNA analog;
    binding the immobilizable tag of the peptidyl moiety of said peptidyl-tRNA to a solid support; and
    detecting the presence of said aminoacyl-tRNA on said solid support as an indication of peptidyl transferase activity.

* * * * *